United States Patent [19]

Curtis et al.

[11] Patent Number: 4,913,894
[45] Date of Patent: Apr. 3, 1990

[54] APPETITE SUPPRESSANT DENTIFRICE

[75] Inventors: John P. Curtis, Piscataway; Susan E. Wieckowski, Iselin; Karen J. De Pierro, Piscataway, all of N.J.

[73] Assignee: Colgate-Palmolive Company, New York, N.Y.

[21] Appl. No.: 346,423

[22] Filed: May 1, 1989

Related U.S. Application Data

[63] Continuation of Ser. No. 96,184, Sep. 11, 1987, abandoned.

[51] Int. Cl.$^4$ .......................... A61K 7/16; A61K 7/26
[52] U.S. Cl. ........................ 424/49; 58/514; 514/817; 514/901; 514/910
[58] Field of Search ................... 424/48–58; 514/910, 817, 901

[56] References Cited

U.S. PATENT DOCUMENTS

| | | | |
|---|---|---|---|
| 2,883,286 | 4/1959 | Musser | 99/139 |
| 2,977,231 | 3/1961 | Fox et al. | 99/79 |
| 3,863,006 | 1/1975 | Hodosh | 424/49 |
| 4,023,712 | 5/1977 | Babiak et al. | 222/175 |
| 4,091,090 | 5/1978 | Sipos | 424/45 |
| 4,315,947 | 2/1982 | Todd et al. | 426/250 |
| 4,357,318 | 11/1982 | Shah et al. | 424/49 |
| 4,497,798 | 2/1985 | Lambert | 424/153 |
| 4,627,978 | 12/1986 | Lynch | 424/54 |
| 4,639,367 | 1/1987 | Markles | 424/45 |
| 4,645,662 | 2/1987 | Nakashima et al. | 424/49 |

FOREIGN PATENT DOCUMENTS

| | | |
|---|---|---|
| 999238 | 11/1976 | Canada . |
| 29332 | 5/1981 | European Pat. Off. ............ 424/57 |
| 2142765 | 2/1973 | France . |

OTHER PUBLICATIONS

Jacobs, M. A. Purf. & Ess. Oil Rev. 61:389 391 393, May 1953, 469, 471 June 1953 "How to Flavor Toothpaste", Flavoring Mouth Washes.
Jean Seligman Newsweek Jul. 16, 1984, p. 86, Health "Is Good Taste Fattening?".
Susan S. Schiffman "Taste and Smell in Disease", Part 2 New England Jurnal of Medicine vol. 308, No. 22, pp. 1337–1343 Jun. 2, 1983.
Suplee "Heavyweights, Let Us Spray" Washington Post, D1, D9 Jan. 1987.
Weintraub "Scentimental Journeys" OMNI, Apr. 1986 52,114,116.
Allen C. A. 52:9524 D (1958).
Koedderman C. A. 78:128425v(1973)CA 86:60560t (1977).
Akkerman CA. 79:351434 (1973).
Murphy CA. 82:160231x(1975).
Niazi et al. CA. 106:144020m (1987).
Naim et al, CA.104:33423j (1986) Kobayashi CA.106:193276h (1987).

*Primary Examiner*—Shep K. Rose
*Attorney, Agent, or Firm*—Robert L. Stone; Murray M. Grill

[57] ABSTRACT

An appetite suppressant oral composition containing Benzocaine, high impact flavor and a sweetening agent, in the form of a dental cream or a mouthspray. A novel method of reducing appetite and thereby intended for controlling weight of consumers, which comprises applying to the oral cavity a high impact flavor in a dentrifrice or mouthspray.

4 Claims, No Drawings

APPETITE SUPPRESSANT DENTIFRICE

This is a continuation of application Ser. No. 096,184 filed 9-11-87, now abandoned.

BACKGROUND AND PRIOR ART

The present invention relates to the formulation of an appetite suppressant oral composition in the form of a dentifrice and mouthspray comprising as essential ingredients Benzocaine, a high impact flavor and a sweetening agent, which coacts to control the appetite and permit reduction in body weight by simply brushing or spraying before or after meals, preferably before meals.

It has been found that the combination of about 0.075–1.5% by weight Benzocaine, about 0.5–1.5% by weight of a high impact flavor, such as chocolate chip mint, and about 0.2–0.6% sweetening agent functions as an appetite suppressant agent in a dentifrice formulation. This unexpected use of present novel dentifrice to suppress appetite and promote weight loss provides a new secondary benefit to the oral hygiene function of a dentifrice.

Current products to suppress appetite and control weight are generally drugs with undesirable side effects, often with a propensity to be addictive; whereas present novel appetite suppressant dentifrice provides a non-pharmacological means to suppress appetite.

There are many appetite suppressant products on the market, both prescription items and over the counter products. Most of these products act as central nervous system stimulants, such as amphetamines, or have a similar mechanism of action. Many of the over the counter products, such as Acutrin, Dexatrim, Appedrine, etc. contain Phenylpropanolamine HCl±Caffeine. Ayds, another well known appetite suppressant product, is a caramel candy containing Benzocaine.

U.S. Pat. No. 3,856,942 also discloses an appetite control composition which is readily ingested, comprising a candy base of sucrose and maltose, caffeine, Benzocaine, vitamins and optionally flavors including quinine to reduce the sweetness of the sucrose and maltose. This composition is preferably a slow-dissolving hard candy or tablet, but may also be in the form of gum drops, chocolate bars or drops, cotton candy, lozenges or gelatin desserts, all of which are ingestible.

Oral compositions, containing Benzocaine for temporary relief of pain in the oral cavity are well known products on the market such as Anbesol gel, a liquid comprising phenol, alcohol and benzocaine; Chloroseptic losenges containing Benzocaine, corn syrup, glycerine, sucrose and flavor for temporary relief of sore throat pain; and Hurricain Topical anesthetic aerosol spray containing 20% benzocaine to control oral pain.

Benzocaine is also an ingredient in otic solutions useful as analgesic-decongestant ear drops; and in hemorrhoid ointment suppositories to shrink the inflamed hemorrhoid tissue and to relieve pain.

Benzocaine is recognized as safe and effective for oral use as an over-the-counter (OTC) anorectic (weight control) in a dose of 3 to 15 mg. in gum, lozenges or candy. The benzocaine controls appetite by numbing the oral mucous membranes as disclosed in the *Federal Register*, vol. 47, No. 39, Feb. 26, 1982, pp. 8473 and 8474.

However, none of the above cited prior art discloses an appetite suppressant dentifrice formulation to control weight, comprising a suppressant agent containing Benzocaine, a high impact flavor and a sweetening agent, in a dental vehicle which may be in the form of a dental cream or a mouth spray. The concept of a dentifrice formulation containing an appetite suppressant agent is novel.

SUMMARY OF THE INVENTION

It has now been found that an appetite suppressant dentifrice intended to effect weight control can be formulated by adding an appetite suppressant agent comprising about 0.075–1.5% and preferably 0.15 to 1.5% by weight Benzocaine, about 0.5–1.5 and preferably 0.5–1% by weight of a high impact flavor, and about 0.2–0.6% by weight of a sweetening agent, to a dental vehicle, which may be in the form of a dental cream or toothpaste or mouthspray. It has been found that the coaction of the active ingredients, namely, the high impact (intense) flavor such as chocolate chip mint, cherry, and the like, which satisfies the cravings for sweets without adding weight; with the sweetening agent which synergistically improves the taste of the flavor; and with the Benzocaine which provides temporary topical anesthetic action on nerve endings in the oral mucosa and tongue to decrease one's ability to detect degrees of sweetness and reduce the craving for foods intended to lead to beverages. Appetite suppression and weight control can be obtained by brushing the teeth or spraying the mouth, before or after, preferably before each meal, on a regular basis such as three times/day with the toothpaste or mouthspray in accordance with present invention, preferably before meals.

Accordingly, a primary object of present invention is to provide an appetite suppressant dentifrice formulation by the incorporation of an appetite suppressant agent comprising Benzocaine, a high impact flavor and a sweetening agent.

Another object of this invention is to provide an appetite suppressant dentifrice in the form of a dental cream and mouthspray for use preferably prior to meals, to promote weight loss.

Still another object of present invention is to provide a dentifrice to suppress appetite and promote weight loss as a new secondary benefit to a dentifrice.

Another object of present invention is to provide a novel essentially non-ingested composition to suppress appetite and promote weight loss via a dentifrice formulation.

Another object of present invention is to provide a novel method of reducing appetite and controlling weight by administering a high impact flavor in a dentifrice or mouth spray on a regular basis.

Additional objects, advantages and novel features of the invention will be set forth in part in the description which follows, and in part will become apparent to those skilled in the art upon examination of the following or may be learned by practice of the invention. The object and advantages of the invention may be realized and attained by means of the instrumentalities and combinations particularly pointed out in the appended claims.

To achieve the foregoing and other objects in accordance with the present invention, as embodied and broadly described herein, the novel appetite suppressant dental cream or mouthspray of this invention comprises a dental vehicle, and an appetite suppressant agent comprising about 0.075–1.5% Benzocaine, about 0.5–1.5% by weight of a high impact flavor and about 0.2–0.6% by weight of a sweetening agent.

More specifically, present invention relates to an appetite suppressant oral formulation to promote weight loss comprising an appetite suppressant agent comprising 0.15 to 1.5% by weight Benzocaine, 0.5-1% by weight of a high impact synthetic flavor composition selected from the group consisting of chocolate chip mint, chocolate, cherry, cheese cake and devil's food cake, and about 0.2-0.6% by weight of a sweetening agent, in a dental vehicle comprising about 65-95% of a liquid vehicle comprising about 10-75% by weight of a mixture of humectants containing a major amount of sorbitol, about 3-43% water and about 0-43% ethanol by weight of the total composition.

The present appetite suppressant as dentifrice in the form of a dental cream including toothpaste and dental gel contains about 65-75% by weight of a mixture of humectants containing a major amount of sorbitol, about 0.35-2% by weight gelling agent, about 1.0-2.0% by weight anionic or nonionic surfactant, and about 18-25% by weight of a water insoluble dental polishing agent.

The liquid dental vehicle of present appetite suppressant oral formulation in the form of a mouthspray consists essentially of about 80-85% of a mixture of ethanol and water, preferably in a weight ratio range of about 3.5:4.5 to about 4.5:3.5, most preferably about 1:1. It preferably contains about 10-15% by weight of a mixture of humectants including sorbitol, and about 1-2% by weight of an anionic or nonionic surfactant. All of the aforesaid preferred ingredients are compatible with the appetite suppressant combination of Benzocaine, high impact flavor and sweetening agent.

Benzocaine (ethyl p-aminobenzoate), a well known topical local anesthetic, sparingly soluble in water but soluble in alcohol and ether, is in the form of white or colorless, odorless crystals or white crystalline-powder and has a melting point of about 90° C. The formula for Benzocaine is p—$NH_2C_6H_4COOC_2H_5$. It has been used in powders, ointments and lotions for relief of pain of burns, pruritus, etc. in sunscreens, and as a local anesthetic. It is non-toxic. Benzocaine may be prepared by reducing ethyl p—nitrobenzoate or by esterifying paramidobenzoic acid with ethyl alcohol, or by other known methods in the art. Despite its sparing water solubility, it is capable of passing through mucous membranes to a sufficient extent to reduce the sensation of a craving for food, i.e. it is an appetite suppressant.

The amount of Benzocaine effective in numbing the desire for food and coact with the high impact flavor and sweetening agent to suppress appetite in the oral composition is about 0.075 to 1.5% and preferably about 0.15 to 1.5% by weight.

Another essential component in the appetite suppressant agent combination is the high impact flavor which is an intense flavor including chocolate chip mint, chocolate, cherry, cheese cake, and devils food cake, and other such intense flavors. The high impact flavor is a blend of a number of components so that the resultant mixture is a well-rounded, smooth flavor with an intense immediate initial impact and with a lasting pleasant aftertaste (e.g. at least about 45-60 seconds). The artificial chocolate flavor used in present novel dentifrice formulations referred to as Bell chocolate is obtained from Bell Flavors and Fragrances, Inc. and is described as a dark yellow to yellow-brown colored clear liquid having the flavor and aroma typical of chocolate, having a specific gravity of 1.095-0.995 and a refractive index of 1.4417-1.4517 at 25° C. The chocolate chip mint flavor is a combination of 70% Bell chocolate, 25% peppermint red and 5% menthol. The artificial cheesecake flavor is a mixture of 39.1% propylene glycol, 20% benzyl alcohol, 8% vanillin, 8% lemon oil and 6% butter acids, as the major ingredients. The artificial cherry flavor utilized in present novel appetite suppressant dentifrice is a mixture of 39.5% benzaldehyde, 16% tolyl aldehyde, 12% amyl butyrate, 8% amyl acetate and 4.5% ethyl butyrate as the major ingredients. Other food grade artifical flavors may be used provided they are intense flavors of high initial impact with a lasting pleasant aftertaste.

The amount of present novel high impact flavor effective in satisfying the urge for sweets without adding weight, and to suppress appetite is about 0.5 to 1.5% and preferably about 0.5 to 1.0% by weight of the dentifrice composition, depending on the type of flavor, type of base and consumer acceptance.

Another essential component in the appetite suppressant agent combination is a sweetening agent which improves the taste of the flavor, in the weight ratio of about 5:1 to 1.3:1, and preferably 2.5:1 to 2:1 of flavor:sweetening agent.

The sweetening agent which includes sucrose, lactose, maltose, stevioside, perillartine, acetosulfam, sodium cyclamate and sodium saccharin, coacts with the flavoring agent in the production of a sweet, intense pleasant taste. The preferred sweetening agent is saccharin. The amount of sweetening agent effective in assisting the present novel flavor formulation in sweetening the dentifrice is typically about 0.2-0.6% by weight of the dentifrice composition.

The dental vehicle in accordance with the invention comprises about 65-95% of a liquid vehicle comprising about 3-43% water and about 10-75% by weight of the mixture of humectants selected from the group consisting of sorbitol, glycerin and polyethylene glycol, and 0-43% ethanol. The sorbitol is the major humectant ingredient because of its sweet taste. Minimal amounts of polyethylene are used due to its bitter taste. A mixture of sorbitol and glycerin is preferred. In the toothpaste, dental gel or dental cream, the humectant constitutes about 65-75% by weight of the dentifrice and the water content is about 3-5% by weight of the dentifrice. In the mouthspray the humectant content constitutes about 10 to 15% by weight of the composition, and the remaining liquid content constitutes about 80-85% of a mixture of water and ethanol, preferably in equal amounts. The total liquid content will generally be about 65 to 95% by weight of the dentifrice formulation.

It is preferred to use a gelling agent in dental creams or gels, such as the natural and synthetic gums and gum like materials, for example, Irish moss, gum tragacanth, cellulose gums such as methyl cellulose, carboxymethyl cellulose, hydroxyethyl cellulose, hydroxmethyl cellulose, polyvinylpyrrolidone, hydrophilic collodial carboxyvinyl polymers, such as those sold under the trademark Carbopol 934 and 940 and synthetic silicated clays such as those sold under the trademark Laponite CP and Laponite SP. These grades of Laponite have the formula $(Si_8Mg_5Li_{0.6}O_{24})^{0.6-}Na^{0.6+}$. The gelling agent constitutes about 0.35-2.0% by weight of the dentifrice formulation.

The dental cream formulations will generally also include a dentally acceptable, substantially water insoluble, polishing agent of the type commonly employed in dental creams. Representative polishing agents include, for example, dicalcium phosphate, tricalcium phosphate, insoluble sodium metaphosphate, aluminum hydroxide, including hydrated alumina, colloidal silica, precipitated silica and magnesium carbonate, calcium carbonate, calcium pyrophosphate, and bentonite, including suitable mixtures thereof. It is preferred to use silica-containing polishing agents such as amorphous hydrated silicon dioxide ($SiO_2$ $H_2O$), known as Zeodent/Zeofree/Zeosyl/Zeothix obtainable from J. M. Huber Corporation, which is in the form of a white, odorless powder having an average particle size of 8-10 micrometers and a density of 2 g/ml. at 25° C. Amorphous silica, also called silica gel and silicic acid, is also obtainable from W. R. Grace & Co. as Sylodent 704 which is a dry white powder having an average particle size of 4 microns and a specific gravity of 2.1. Sylox$^{(R)}$ is another amorphous silica provided by W. R. Grace & Co., in the form of a dry white powder having an average size of 1.5-12 microns. The preferred siliceous containing polishing agent constitutes about 18-25% by weight of the dental cream formulations.

When the dental cream is a visually clear gel or opacified gel, a polishing agent of colloidal silica, such as those sold under the trademark Syloid as Syloid 72 and Syloid 74 or under the trademark Santocel as Santocel 100 and synthetic alkali metal aluminosilicate complexes (including silica containing combined alumina) may be particularly useful. They have refractive indices close to the refractive indices of gelling agents-liquid systems commonly used in dentifrices (which generally include humectants such as glycerine and sorbitol).

The polishing agent content is generally in amounts from about 18-35% by weight in a dental cream.

Organic surface-active agents are preferably used in the composition of the present invention to assist in achieving thorough and complete dispersion of the compositions of the present invention throughout the oral cavity and render the said compositions more cosmetically acceptable. The organic surface-active agent material may be anionic or nonionic, in nature, and it is preferred to employ as the surface-active agent a detersive material which imparts to the composition detersive and foaming properties. Suitable anionic surfactants include water-soluble salts of higher fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, higher alkyl sulphoacetates, higher fatty acid esters of 1,2-dihydroxy propane sulphonates, olefin sulphonates and the like.

Other particularly suitable surface active materials include nonionic agents such as condensates of sorbitan monostearate with approximately 20 moles of ethylene oxide, condensates of ethylene oxide with propylene oxide, condensates of propylene glycol (Pluronics); condensation products of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to 1600 and containing 40% to 80% by weight of ethylene oxide, with an α-olefin oxide to polyhydric alcohol mole ratio in the range of 1:1 to 1:3.

The amount of anionic or nonionic surfactant constitutes about 1-2% by weight of the dentifrice formulation.

The dentifrice of this invention may also contain conventional additional ingredients such as coloring or whitening agents and preservatives. These additional ingredients may each be added to the dentifrice in minimal amounts of up to 5% by weight, and preferably up to 1%, provided they do not interefere with the appetite suppressant and compatibility properties of the finished product.

The dentifrice of this invention is prepared by conventional methods of making toothpaste and/or dental creams or dental gels. More specifically, the gelling agent such as a cellulose gum is dispersed in glycerine, to which is added an aqueous solution containing the sweetening agent such as saccharin and the sodium benzoate preservative, followed by the addition of sorbitol and mixing for a period of about 20 minutes to hydrate the gum, mixing the gum mixture with the polishing agent in a mixer under a vacuum of 28-30 inches of pressure and lastly adding to said vacuum mixer the flavor, the surfactant and Benzocaine, and mixing for a period of about 15 minutes, and tubing the final mixture.

The mouthspray is prepared by mixing the liquid components water, ethanol, sorbitol and glycerin and adding with additional mixing the surfactant, flavor, Benzocaine and sweetening agent, and packaging the final liquid composition in a suitable container provided with a spray device when used as a mouthspray.

In the practice of this invention to suppress appetite and control weight and simultaneously promote oral hygiene, the dentifrice according to this invention is applied regularly to the oral cavity. by brushing the teeth or spraying the mouth for 30-90 seconds, at least three times a day either after or before meals, preferably prior to eating meals.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLES 1 AND 2

| APPETITE SUPPRESSANT DENTAL CREAM | | |
|---|---|---|
| INGREDIENTS | 1 Percent | 2 Percent |
| Sorbitol | 45.80 | 44.45 |
| Glycerin | 25.00 | 25.00 |
| Sylodent 704 | 20.00 | 20.00 |
| Deionized water | 3.00 | 3.00 |
| Polyethylene Glycol 600 | 3.00 | 3.00 |
| POE 40 Sorbitan Diisostearate | 1.00 | 1.00 |
| Chocolate Chip Mint | 0.50 | 0.50 |
| Titanium Dioxide | 0.50 | 0.50 |
| Sodium Benzoate | 0.50 | 0.50 |
| Sodium Carboxyethyl Cellulose | 0.35 | 0.35 |
| Sodium Saccharin | 0.20 | 0.20 |
| Benzocaine | 0.15 | 1.50 |
| pH | 6.26 | 6.3 |

The sodium carboxyethyl cellulose is dispersed in the glycerine, and the sodium benzoate and saccharin is dissolved in the water prior to mixing the water solution with the glycerin dispersion. Sorbitol is added to above mixture and mixed for twenty minutes to hydrate the cellulose gum. The gum mixture is added to the silica in a mixer capable of pulling a vacuum of 28-30 inches. The flavoring composition, the POE 40 sorbitan diisostearate and Benzocaine are added to the above mixture in the mixer under vacuum and mixed for another 15 minutes. The final dentifrice has an intense chocolate minty taste which satisfies the consumers' desire for sweets, and simultaneously suppresses the appetite for additional food. This dentifrice is prepared at room temperature. A 1 gram sample of dental cream containing 0.15% Benzocaine will deliver 1.5 mg of benzocaine; 1.5% benzocaine will deliver 15 mg Benzocaine.

EXAMPLE 3

APPETITE SUPPRESSANT MOUTHSPRAY

| INGREDIENT | % |
| --- | --- |
| Ethanol (90 Proof) | 41.75 |
| Deionized Water | 41.75 |
| Sorbitol | 8.50 |
| Glycerine | 3.00 |
| POE 40 Sorbitan Diisostearate | 1.50 |
| Chocolate Chip Mint | 1.50 |
| Benzocaine | 1.50 |
| Na Saccharine | 0.50 |

The ethanol, water, sorbitol and glycerin are mixed, followed by the sequential addition with mixing of the flavor composition, the POE 40 sorbitan diisostearate, saccharin and Benzocaine, at room temperature. The final product is packaged in any suitable container provided with a spray mechanism. This mouthspray also provides an intense chocolate mint taste and is equally effective as an appetite suppressant as the dental cream. One of the advantages of the mouthspray is that one need not carry a toothbrush.

EXAMPLE 4

DENTAL CREAM

| INGREDIENTS | % |
| --- | --- |
| Sorbitol | 42.45 |
| Glycerine | 25.00 |
| Sylodent 704 | 22.00 |
| Deionized Water | 3.00 |
| Polyethylene Glycol 600 | 3.00 |
| Sorbitan Diisostearate | 1.00 |
| Chocolate Chip Mint | 0.50 |
| Titanium Dioxide | 0.50 |
| Sodium Benzoate | 0.50 |
| Sodium Carboxymethyl Cellulose | 0.35 |
| Sodium Saccharin | 0.20 |
| Benzocaine | 1.50 |

EXAMPLES 5-7

APPETITE SUPPRESSANT DENTAL CREAMS

| INGREDIENTS | PERCENT 5 | 6 | 7 |
| --- | --- | --- | --- |
| Glycerine | 25.00 | 25.0 | 25.0 |
| Na Saccharin | 0.50 | 0.3 | 0.2 |
| Na Carboxymethyl cellulose | 0.35 | 0.35 | 0.35 |
| NaBenzoate | 0.50 | 0.5 | 0.5 |
| TiO2 | 0.50 | 0.5 | 0.5 |
| PEG 500 | 3.00 | 3.0 | 3.0 |
| Deionized Water | 3.00 | 3.0 | 3.0 |
| Sorbitol | 44.875 | 42.25 | 42.25 |
| Sylodent 704 | 20.0 | 22.0 | 22.0 |
| Flavor-Chocolate Chip Mint | — | — | 0.5 |
| Flavor-Cheesecake | — | 0.6 | — |
| Flavor-Chocolate | 1.00 | — | — |
| Sodium lauryl sulfate(SLS) | 1.20 | — | 1.20 |
| Benzocaine | 0.075 | 1.5 | 1.5 |
| POE 40 sorbitan diiosstearate | — | 1.0 | — |
| pH | 6.3 | 6.4 | 6.5 |

The glycerin, saccharin, sodium carboxymethyl cellulose and benzoate are mixed together. The polyethylene glycol 600, water, sorbitol and titanium dioxide are added and mixed to form a mixture which is added to the silica polishing agent and mixed for 20 minutes. To this mixture is added the flavor, the anionic (SLS) or nonionic (POE) surfactant and the benzocaine and mixed for an additional 15 minutes.

The dental creams have intense flavor and suppress the appetite of the consumer after brushing therewith. This provides a harmless topical means of controlling weight without ingesting drugs, troches, losenges, gums, or the like.

Variations in the above formulations may be made. For example, other food grade anionic or nonionic surfactants may be substitued for the sodium lauryl sulfate or polyoxyethylene sorbitan diiostearate surfactants. Similarly, other dental polishing agents may be substituted for the specific silica polishing agent in the specific examples. Likewise, other high impact or intense flavoring composition may be used in lieu of the chocolate chip mint or cheesecake flavors, such as chocolate, cherry, devils food cake and the like.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. In the art of providing temporary topical anesthetic action on nerve endings in the oral mucosa and tongue to decrease one's ability to detect degrees of sweetness and reduce the craving for food and beverages with effective appetite suppressant amounts of benzocaine, the improvement which consists essentially of brushing the teeth before meals, on a regular basis, with an appetite suppressant toothpaste or dental cream essentially containing (A) 0.075-1.5% by weight benzocaine, and (B) about 0.5-1.5% by weight of an intense high impact synthetic or artificial chocolate chip mint or chocolate, artificial cherry, artificial cheesecake and artificial devils food cake flavor, each having an intense immediate initial impact and at least about a 45 to 60 seconds lasting pleasant after-taste effective to satisfy the cravings for sweets without adding weight, and (C) about 0.2 to 0.6% by weight of a sweetening agent effective to coact with said flavoring agent to produce a sweet intense pleasant taste.

2. The method of reducing appetite according to claim 1, wherein the weight ratio of the high impact flavor to the sweetening agent is about 5:1 to 1.3:1.

3. The method of reducing appetite according to claim 1, wherein the ratio of the high impact flavoring composition:sweetening agent is 2.5:1 to 2:1.

4. The method of reducing appetite according to claim 1, wherein the sweetening agent is saccharin.

* * * * *